United States Patent [19]

Oka

[11] Patent Number: 5,785,652
[45] Date of Patent: Jul. 28, 1998

[54] PHYSICAL-INFORMATION ABNORMALITY INFORMING ENDOSCOPE

[75] Inventor: Tohru Oka, Ichinomiya, Japan

[73] Assignee: Colin Corporation, Komaki, Japan

[21] Appl. No.: 710,139

[22] Filed: Sep. 13, 1996

[51] Int. Cl.$^6$ .................................................. A61B 5/00
[52] U.S. Cl. ........................... 600/342; 600/325; 600/341; 600/486; 600/500; 600/101
[58] Field of Search .............................. 128/630, 632, 128/633, 666, 668, 672, 677, 681, 687, 690, 701, 706, 903; 600/101, 103, 109, 113, 300, 309, 310, 479, 481, 485, 500; 601/46

[56] References Cited

U.S. PATENT DOCUMENTS

| | | | |
|---|---|---|---|
| 3,565,058 | 2/1971 | Mansfield | 128/701 |
| 3,732,868 | 5/1973 | Willens et al. | 128/701 |
| 4,510,943 | 4/1985 | Miyamae | 128/680 |
| 4,566,461 | 1/1986 | Lubell et al. | 128/668 |
| 4,566,463 | 1/1986 | Taniguchi et al. | 128/666 |
| 4,653,498 | 3/1987 | New, Jr. et al. | 128/666 |
| 4,998,282 | 3/1991 | Shishido et al. | |
| 5,099,854 | 3/1992 | Choi | 128/690 |
| 5,152,708 | 10/1992 | Claugus et al. | 601/46 |
| 5,282,475 | 2/1994 | Urbach et al. | 128/731 |
| 5,319,355 | 6/1994 | Russek | 128/903 |
| 5,351,677 | 10/1994 | Kami et al. | |
| 5,398,685 | 3/1995 | Wilk et al. | 128/664 |

FOREIGN PATENT DOCUMENTS

| | | |
|---|---|---|
| 3838396 | 5/1990 | Denmark . |
| 0566681 | 10/1993 | European Pat. Off. . |
| 0571827 | 12/1993 | European Pat. Off. . |
| 2284060 | 5/1995 | United Kingdom . |

*Primary Examiner*—Jennifer Bahr
*Assistant Examiner*—Bryan K. Yarnell
*Attorney, Agent, or Firm*—Oliff & Berridge, PLC

[57] ABSTRACT

An apparatus for informing an operator of an abnormality of a physical information obtained from a living subject, including a physical-information obtaining device which obtains the physical information from the subject via an endoscope and outputs a physical-information signal representing the obtained physical information, a signal converting device which converts the physical-information signal into an analog speech signal having a waveform representing a speech corresponding to the obtained physical information, a speech outputting device which outputs the speech represented by the speech signal, a judging device for judging whether the obtained physical information represented by the physical-information signal is abnormal, and a frequency shifting device which shifts, when the judging means makes a positive judgment, frequencies of the speech output by the speech outputting device, so that the operator is informed of the abnormality of the physical information obtained from the subject.

18 Claims, 3 Drawing Sheets

PHYSICAL-INFORMATION ABNORMALITY INFORMING ENDOSCOPE

BACKGROUND OF THE INVENTION

1. Field of the Invention

The present invention relates to an apparatus for informing an operator of an abnormality of physical information which is obtained from a living subject by a physical-information obtaining device.

2. Related Art Statement

When a medical worker such as a doctor carries out, using a medical microscope, a surgical operation on a patient or carries out, using an endoscope, an endoscopy on a patient, he or she should concurrently monitor the physical condition of the patient. In order to help the medical worker, there has been used a physical-information abnormality informing device which includes a physical-information obtaining device such as a blood pressure (BP) measuring device, a blood-oxygen-saturation measuring device (i.e., oximeter), or a clinical thermometer, and judging means for judging whether the physical information obtained by the physical-information obtaining device is abnormal. The abnormality informing device further includes an alarming device such as a buzzer which produces, when the judging means makes a positive judgment, an alarm sound, thereby informing the worker of the abnormality of the obtained physical information.

Thus, the above abnormality informing device clearly informs a medical worker of an abnormality of physical information obtained from a patient. However, the patient also hears the alarm sound and may recognize the abnormality. Thus, the patient may feel anxiety about it.

SUMMARY OF THE INVENTION

It is therefore an object of the present invention to provide a physical-information abnormality informing apparatus which clearly informs an operator of an abnormality of physical information obtained from a living subject, without causing the subject to feel anxiety about the physical information obtained from himself or herself.

The above object has been achieved by the present invention. According to a first aspect of the present invention, there is provided an apparatus for informing an operator of an abnormality of a physical information obtained from a living subject, comprising a physical-information obtaining device which obtains the physical information from the subject and outputs a physical-information signal representing the obtained physical information, a signal converting device which converts the physical-information signal into an analog speech signal having a waveform representing a speech corresponding to the obtained physical information, a speech outputting device which outputs the speech represented by the speech signal, judging means for judging whether the obtained physical information represented by the physical-information signal is abnormal, and a frequency shifting device which shifts, when the judging means makes a positive judgment, frequencies of the speech output by the speech outputting device, so that the operator is informed of the abnormality of the physical information obtained from the subject. The frequency shifting device may shift the frequencies of the speech, from a first predetermined frequency range to a second frequency range higher or lower than the first frequency range. Thus, the voice of the speech may be changed from a male voice to a female voice, or vice versa.

The physical-information abnormality informing apparatus in accordance with the first aspect of the invention, can clearly inform, e.g., a medical worker who is concentrating his or her attention on a medical test, treatment or operation, of an abnormality of physical information obtained from a living subject such as a patient. On the other hand, the subject would not recognize the abnormality of physical information obtained from himself or herself and therefore would not feel any anxiety.

According to a preferred feature of the first aspect of the invention, the speech outputting device comprises a speaker. The speaker may comprise a portable speaker which is adapted to be worn on the head of the operator. In this case, the operator is more clearly informed of the abnormality of physical information. In addition, it would be more difficult for the subject to hear the speech output from the portable speaker. Thus, the subject does not feel any anxiety. The portable speaker may be an earphone or a headphone.

According to another feature of the first aspect of the invention, the judging means comprises means for making the positive judgment that the obtained physical information is abnormal, when a measured value as the obtained physical information does not fall within a predetermined normal range.

According to another feature of the first aspect of the invention, the physical-information obtaining device comprises at least one of a blood-pressure measuring device, a blood-oxygen-saturation measuring device, and a heart-rate measuring device.

According to another feature of the first aspect of the invention, the frequency shifting device comprises means for shifting the frequencies of the speech up to higher frequencies, when the judging means makes the positive judgment. In this case, the voice of the speech may be changed from a male voice to a female voice.

According to another feature of the first aspect of the invention, the frequency shifting device comprises means for modulating the speech signal provided by the signal converting device, thereby shifting the frequencies of the speech output by the speech outputting device.

According to another feature of the first aspect of the invention, the abnormality informing apparatus further comprises an endoscope which is operable by the operator for carrying out an endoscopy on the subject.

According to a second aspect of the present invention, there is provided an apparatus for informing an operator of an abnormality of a physical information obtained from a living subject, comprising a physical-information obtaining device which obtains the physical information from the subject and outputs a physical-information signal representing the obtained physical information, judging means for judging whether the obtained physical information represented by the physical-information signal is abnormal, and a portable vibrator which is adapted to be worn on the operator and which produces, when the judging means makes a positive judgment, a vibration which is transmitted to the operator so that the operator is informed of the abnormality of the physical information obtained from the subject.

In the physical-information abnormality informing apparatus in accordance with the second aspect of the invention, the operator on whom the portable vibrator is worn is clearly informed of an abnormality of physical information obtained from a living subject such as a patient, even if the operator is concentrating his or her attention on a medical test, treatment or operation. On the other hand, the subject cannot know the abnormality of physical information obtained from himself or herself and accordingly will not feel any anxiety.

According to a preferred feature of the second aspect of the invention, the portable vibrator comprises means for producing the vibration having a frequency falling within a range of 1 to 100 Hz.

According to another feature of the second aspect of the invention, the portable vibrator comprises an eccentric rotor whose center of gravity is eccentric with respect to an axis of rotation thereof, and an electric motor which rotates the rotor about the axis of rotation.

According to another feature of the second aspect of the invention, the portable vibrator further comprises a wrist band which supports the rotor and the motor and which is adapted to be wound around a wrist of the operator.

According to another feature of the second aspect of the invention, the judging means comprises means for making the positive judgment that the obtained physical information is abnormal, when a measured value as the obtained physical information does not fall within a predetermined normal range.

According to another feature of the second aspect of the invention, the physical-information obtaining device comprises at least one of a blood-pressure measuring device, a blood-oxygen-saturation measuring device, and a heart-rate measuring device.

According to another feature of the second aspect of the invention, the abnormality informing apparatus further comprises an endoscope which is operable by the operator for carrying out an endoscopy on the subject.

According to another feature of the second aspect of the invention, the abnormality informing apparatus further comprises a signal converting device which converts the physical-information signal into an analog speech signal having a waveform representing a speech corresponding to the obtained physical information, a speech outputting device which outputs the speech represented by the speech signal, and a frequency shifting device which shifts, when the judging means makes the positive judgment, frequencies of the speech output by the speech outputting device, so that the operator is informed of the abnormality of the physical information obtained from the subject.

According to another feature of the second aspect of the invention, the abnormality informing apparatus further comprises an speech-output switch which is operable for selectively placing the speech outputting device in a first mode in which the speech outputting device outputs the speech and a second mode in which the speech outputting device does not output the speech.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which.

DETAILED DESCRIPTION OF THE PREFERRED EMBODIMENTS

Figure 1:
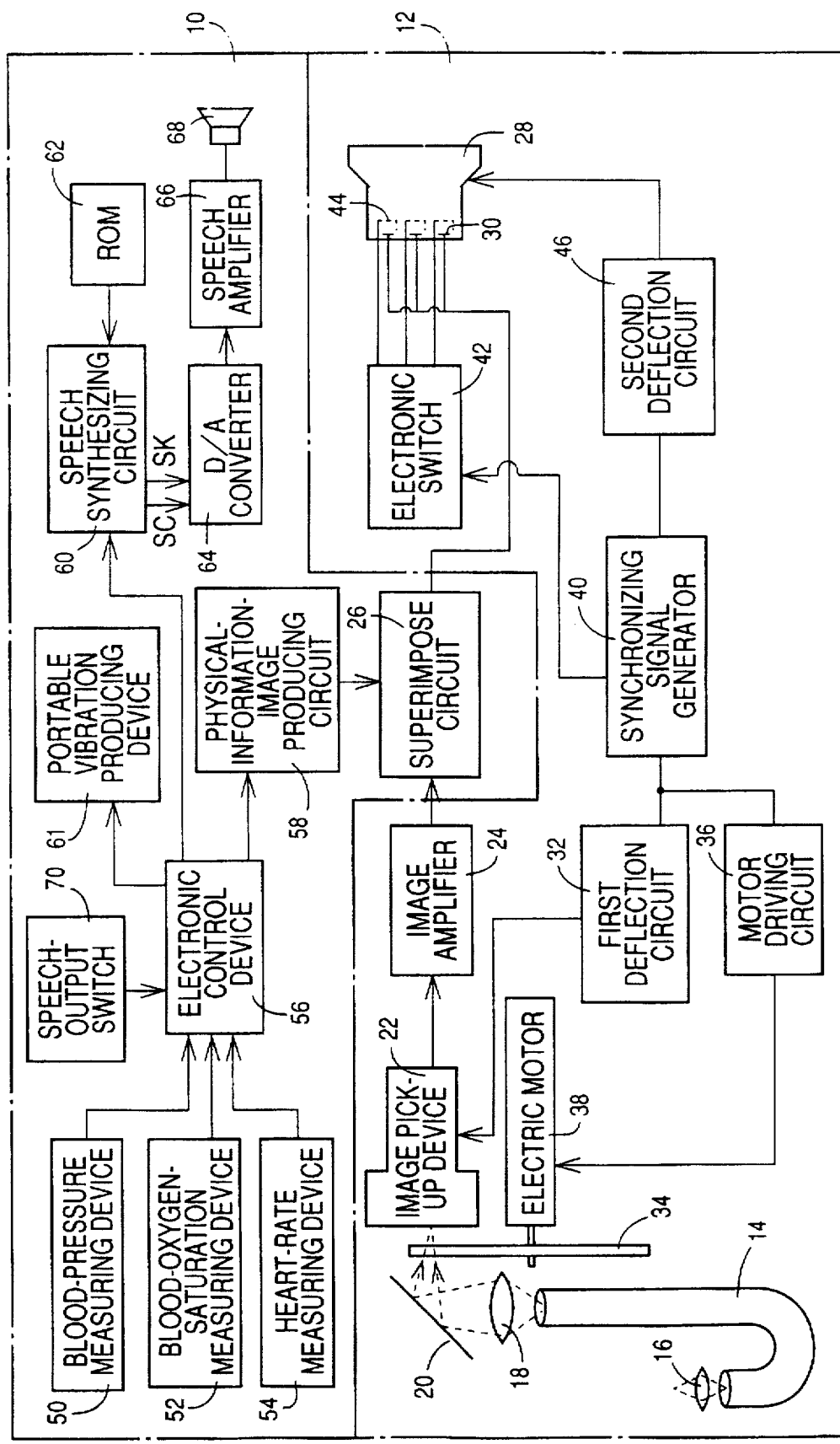
FIG. 1 is a diagrammatic view of an endoscope system including an endoscope apparatus, and a physical-information abnormality informing apparatus to which the present invention is applied.
Figure 2:
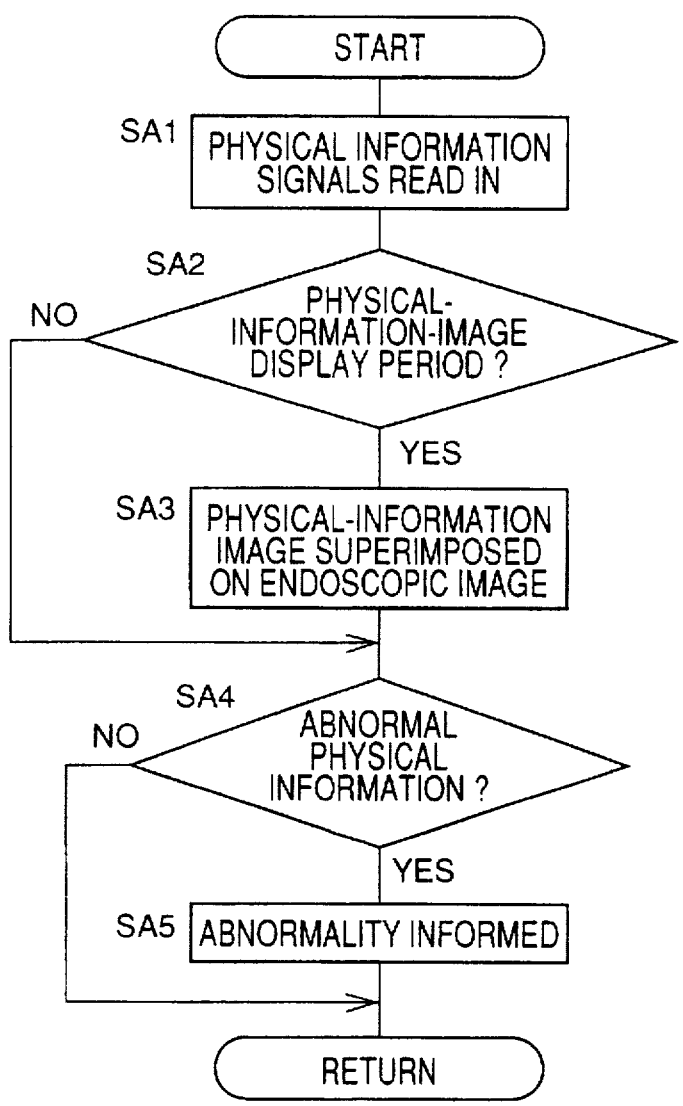
FIG. 2 is a flow chart representing a control program according to which the informing apparatus of FIG. 1 is operated.
Figure 3:
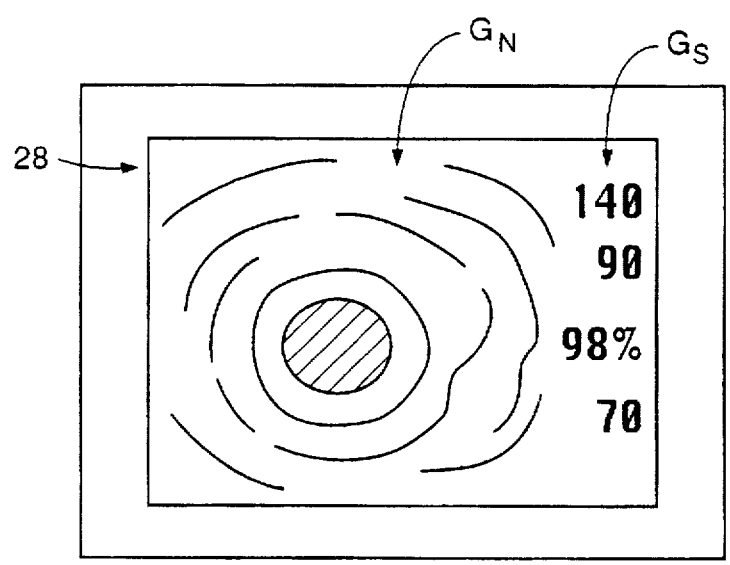
FIG. 3 is a view of an endoscopic image and a physical-information image superimposed on the endoscopic image which are displayed by a color cathode ray tube (CRT) as an image displaying device of the endoscope apparatus of FIG. 1.

Referring to FIGS. 1 through 3, there will be described an endoscope system including an endoscope apparatus 12, and a physical-information abnormality informing apparatus 10 to which the present invention is applied.

As shown in FIG. 1, the endoscope apparatus 12 includes an optical-fiber device 14 including a light guide which transmits an irradiating light generated from a light source (not shown), and an image fiber which transmits an endoscopic image of, e.g., the inner wall of stomach of a patient irradiated by the light. The optical fiber 14 is provided by a bundle of glass fibers each of which has a diameter of several microns, and accordingly has a high flexibility. Thus, the optical fiber 14 can reach an internal, deep portion of the patient via a meandering path such as mouth and esophagus.

The optical fiber 14 transmits the endoscopic image formed on one end face thereof by an object lens 16, to the other end face thereof, so that the endoscopic image is formed on an image pick-up device 22 via an image-forming lens 18 and a reflecting mirror 20. The image pick-up 22 is provided by, e.g., an image orthicon or a CCD (charge-coupled devices) image sensor. The image pick-up 22 produces an endoscopic-image signal representing the endoscopic image obtained by the optical fiber 14, and supplies the endoscopic-image signal to three cathodes (electron guns) 30 of a color cathode ray tube (CRT) 28 via an image-signal amplifier 24 and a superimpose circuit 26. The color CRT 28 provides an endoscopic-image display of the endoscope apparatus 12. The image pick-up 22 outputs, in response to a timing signal supplied from a first deflection circuit 32, scanning-line signals respectively corresponding to scanning lines of the color CRT 28. A three-color filter 34 is provided between the image-forming lens 18 and the image pick-up 22, and is driven or rotated by an electric motor 38 under control of a motor driving circuit 36. Thus, the endoscopic image obtained by the optical fiber 14 is separated into the three primary colors, i.e., red, green, and blue, and each of the frames provided by the endoscopic-image signal output from the image pick-up 22 has one of the three primary colors.

In response to the timing signal supplied from the first deflection circuit 32, a synchronizing signal generator 40 supplies a synchronizing signal to an electronic switch 42 which switches, in response to the synchronizing signal, three control grids 44 of the color CRT 28, from one to another. Thus, the respective electron beams emitted from the three cathodes 30 are switched from one to another, and the red, green, and blue frames provided by the endoscopic-image signal are displayed in turn on the screen of the color CRT 28. Thus, the endoscopic image is seen as a full-color image by an operator. In response to the timing signal from the first deflection circuit 32, a second deflection circuit 46 supplies a deflection signal to a deflection coil of the color CRT 28 to deflect the electron beams emitted from the cathodes 30.

The physical-information abnormality informing apparatus 10 includes a blood-pressure (BP) measuring device 50 which measures a BP value, BP, (mmHg) of the patient on whom the endoscope apparatus 50 is being used; a blood-oxygen-saturation measuring device (i.e., pulse oximeter) 52 which optically measures a blood oxygen saturation, OX, (%) of the patient; and a heart-rate measuring device 54 which measures a heart rate, HR, (/min) of the patient. Each of the three measuring devices 50, 52, 54 produces a physical-information signal (i.e., electric signal) representing the detected physical information, and supplies the signal to an electronic control device 56. In the present embodiment, each of the three measuring devices 50, 52, 54 provides a physical-information obtaining device.

The electronic control device 56 is provided by a microcomputer including a central processing unit (CPU, not shown), a read only memory (ROM, not shown), and a random access memory (RAM, not shown). The CPU processes each of the respective physical-information signals supplied from the three measuring device 50, 52, 54, according to control programs pre-stored in the ROM, by utilizing a temporary-storage function of the RAM, and supplies data indicative of a value as each of the three sorts of physical information, and/or data indicative of an abnormality of each physical information, to each of a physical-information-image-signal producing circuit 58, a speech-signal synthesizing circuit 60, and a portable vibration producing device 61.

The physical-information-image-signal producing circuit 58 produces a physical-information-image signal representing a physical information image including a value (i.e., digits) as each of the respective sorts of physical information obtained by the three measuring devices 50, 52, 54, i.e., BP value BP (mmHg), oxygen saturation OX (%), and heart rate HR (/min). The physical-information-image signal indicates that the physical-information image be displayed in a predetermined area on the screen of the color CRT 28. The superimpose circuit 26 superimposes the physical-information-image signal on the endoscopic-image signal supplied from the image-signal amplifier 24 to the CRT 28, so that the physical-information image is superimposed on the endoscopic image on the screen of the CRT 28. The superimpose circuit 26 is provided by a commercially available superimpose IC (integrated circuit) which is well known in the art and is commonly used for superimposing a number indicative of a current channel and/or a number indicative of a current day time, on a screen image of a CRT.

The abnormality informing apparatus 10 further includes a speech-signal storing ROM 62 which stores, in advance, a plurality of code signals, SC, representing a plurality of sorts of speech, respectively. For example, a code signal $SC_{BP}$ corresponding to blood pressure represents a speech or voice that the systolic BP value of the patient is 140 mmHg and the diastolic BP value is 90 mmHg; a code signal $SC_{OX}$ corresponding to blood oxygen saturation represents a speech that the blood oxygen saturation of the patient is 98%; and a code signal $SC_{HR}$ corresponding to heart rate represents a speech that the heart rate of the patient is 70 per minute. A speech-output switch 70 is manually operable by the operator for selectively placing the abnormality informing apparatus 10 in a speech-output mode in which the apparatus 10 outputs a speech and a silent mode in which the apparatus 10 does not output any speech. With the speech-output switch 70 being switched to the speech-output mode, the speech-signal synthesizing circuit 60 selects one of the code signals which corresponds to a command signal supplied from the control device 56 with respect to each of the obtained three sorts of physical information. The thus selected three code signals $SC_{BP}$, $SC_{OX}$, $SC_{HR}$ are supplied to a digital-to-analog (D/A) converter 64. In addition, the speech-signal synthesizing circuit 60 selects one of a plurality of clock signals, SK, representing different clock frequencies, according to a command signal supplied from the control device 56 with respect to each of the obtained three sorts of physical information. The thus selected three clock signals $SK_{BP}$, $SK_{OX}$, $SK_{HR}$ are supplied to the D/A converter 64.

The D/A converter 64 converts each code signal SC ($SC_{BP}$, $SC_{OX}$, $SC_{HR}$) into an analog speech signal having a waveform representing a speech corresponding to the obtained physical information BP, OX, HR, at the frequency or period represented by a corresponding clock signal SK ($SK_{BP}$, $SK_{OX}$, $SK_{HR}$). Thus, the speech represented by each speech signal has frequencies in a predetermined range corresponding to the frequency represented by a corresponding clock signal SK. Each speech signal is amplified by a speech-signal amplifier 66 and then is supplied to a speaker 68 as a speech outputting device, so that the speaker 68 outputs the speech represented by the speech signal. Thus, the speech-signal synthesis is effected by a so-called pulse code modulation. In the present embodiment, the control device 56, the speech-signal synthesizing circuit 60, the ROM 62, and the D/A converter 64 cooperate with one another to provide a signal converting device which converts each physical-information signal into an analog speech signal having a waveform representing a speech corresponding to the obtained physical information BP, OX, HR.

The portable vibration producing device 61 includes an eccentric rotor (not shown) whose center of gravity is eccentric with respect to an axis of rotation thereof, and an electric motor (not shown) which rotates the rotor about the axis of rotation. The vibrator 61 further includes a wrist band (not shown) which is adapted to be wound around a wrist of the operator and which supports the rotor and the motor. The vibrator 61 produces, according to a command signal supplied from the control device 56, vibration having a low frequency falling within the range of 1 to 100 Hz, preferably, 3 to 60 Hz. The vibration produced by the vibrator 61 is transmitted to the operator to inform him or her of an abnormality of the physical information obtained from the subject.

There will be described the operation of the abnormality informing apparatus 10 constructed as described above, by reference to the flow chart of FIG. 2 which represents a control program pre-stored in the ROM of the control device 56. First, at Step SA1, the CPU of the control device 56 reads in the respective physical-information signals supplied from the three measuring devices 50, 52, 54. Step SA1 is followed by Step SA2 to judge whether it is now within a cyclic physical-information-image displaying duration. The cycle time of this duration is, e.g., 15 seconds, and each duration lasts one third to one fifth of the cycle time.

If a negative judgment is made at Step SA2, the control of the CPU goes to Step SA4. On the other hand, if a positive judgment is made at Step SA2, the control of the CPU goes to Step SA3 to supplies data indicative of a value as each of the respective sorts of physical information obtained by the three measuring devices 50, 52, 54, i.e., BP value BP (mmHg), oxygen saturation OX (%), and heart rate HR (/min), to the physical-information-image-signal producing circuit 58, which produces a physical-information-image signal representing a physical-information image including the value as each of the three sorts of physical information. The superimpose circuit 26 superimposes the physical-information-image signal representing the physical-information image, on the endoscopic-image signal representing the endoscopic image, so that the physicalinformation image, $G_S$, is superimposed on a right-hand end area of the endoscopic image, $G_N$, on the screen of the color CRT 28, as shown in FIG. 3. In FIG. 3, values "140" and "90" shown in the top of the image GS represent a systolic and a diastolic BP value $BP_{SYS}$, $BP_{DIA}$ of the patient, respectively; value "98%" in the middle of the image $G_S$ represents a blood oxygen saturation OX of the patient; and value "70" in the bottom of the image $G_S$ represents a heart rate HR of the patient.

In addition, at Step SA3, if the speech-output switch 70 is set at the speech-output mode, the CPU of the control device 56 supplies, only one time, the data indicative of the value as each of the respective sorts of physical information BP, OX, HR, to the speech-signal synthesizing circuit 60, so that finally the speaker 68 outputs a speech or voice corresponding to each of the three sorts of physical information BP, OX, HR. At Step SA3, the synthesizing circuit 60 supplies, to the D/A converter 64, a clock signal, $SK_{LF}$, indicative of the lower one of two different frequencies, with respect to each of the three sorts of physical information BP, OX, HR, i.e., three sorts of code signals $CS_{BP}$, $SC_{OX}$, $SC_{HR}$, so that the speaker 68 outputs each speech in a low voice like a man. Step SA3 is followed by Step SA4.

At Step SA4, the CPU of the control device 56 judges whether each of the systolic and diastolic BP values, blood oxygen saturation OX, and heart rate HR of the patient read in at Step SA1 is abnormal. This judgment is made by judging whether a value as each physical information falls within a corresponding predetermined normal range. A negative judgment is made at Step SA4 if the value as each physical information falls within the corresponding predetermined normal range. In this case, the present routine is ended. On the other hand, a positive judgment is made at Step SA4 if the value as each physical information does not fall within the corresponding predetermined normal range. In the latter case, the control of the CPU goes to Step SA5. Thus, Step SA4 corresponds to abnormality judging means.

At Step SA5, the CPU of the control device 56 supplies a drive signal to the portable vibration producing device 61 to produce vibration so that the vibration is transmitted to the operator. In addition, at Step SA5, if the speech-output switch 70 is set at the speech-output mode, the CPU of the control device 56 supplies the data indicative of the value as each of the respective sorts of physical information BP, OX, HR, to the speech-signal synthesizing circuit 60, so that finally the speaker 68 outputs a speech or voice corresponding to each of the three sorts of physical information BP, OX, HR. At Step SA5, however, the CPU controls the synthesizing circuit 60 to supply, to the D/A converter 64, a clock signal, $SK_{HF}$, indicative of the higher one of the two different frequencies, with respect to each of the three sorts of physical information BP, OX, HR or the three sorts of code signals $CS_{BP}$, $SC_{OX}$, $SC_{HR}$, so that the speaker 68 outputs each speech in a loud voice like a woman. Thus, the control device 56, the synthesizing circuit 60, the D/A converter, and Step SA5 cooperate with one another to provide a frequency shifting device.

As is apparent from the foregoing description, in the present embodiment, at Step SA1, the BP measuring device 50, the blood-oxygen-saturation measuring device 52, and the heart-rate measuring device 54 measure, as physical information, a systolic and a diastolic BP value BP, a blood oxygen saturation OX, and a heart rate HR of the patient, respectively, and at Step SA4 the control device 56 judges whether each of the physical-information values BP, OX, HR is abnormal. If a positive judgment is made at Step SA4, at Step SA5 the control device 56 controls the speech-signal synthesizing circuit 60 and the D/A converter 64 to modify the speech signal so that the frequencies of the speech or the speech output from the speaker 68 are changed or shifted up to higher frequencies. Thus, even a medical worker such as a doctor who is engaged in operating the endoscope apparatus 12 or the optical-fiber device 14, can clearly recognize the abnormality of the physical information obtained from the patient under the endoscopy. On the other hand, the patient feels no anxiety even if the frequencies of the speech corresponding to the obtained physical information is shifted.

In addition, in the present embodiment, if at Step SA4 a positive judgment is made, at Step SA5 the control device 56 controls the portable vibration producing device 61 being worn on the medical worker to produce vibration so that the produced vibration is transmitted to the worker. Thus, the worker can more clearly recognize the abnormality of the physical information obtained from the patient under the endoscopy. On the other hand, the patient feels no anxiety because the patient does not perceive the vibration produced from the portable vibrator 61.

While the present invention has been described in its preferred embodiment, the present invention may otherwise be embodied.

For example, while in the illustrated embodiment the medical worker is informed of an abnormality of physical information by both the speaker 68 and the portable vibrator 61, it is possible to omit one of the two elements 68, 61.

Although in the illustrated embodiment the speaker 68 is built in the abnormality informing apparatus 10, it is possible to replace the built-in speaker 68 with a portable speaker such as a headphone or an earphone which is worn on the head or ears of an operator. In the latter case, the operator can more clearly be informed of an abnormality of physical information obtained from the patient under the endoscopy, and the patient feels no anxiety because he or she can hardly hear the speech output from the portable speaker.

While in the illustrated embodiment the three physical-information obtaining devices, i.e., BP measuring device 50, oxygen-saturation measuring device 52, and heart-rate measuring device 54 are employed, it is possible to employ only one or two of the three devices 50, 52, 54 or employ one or more other devices for measuring one or more other sorts of physical information, such as respiration rate or arrhythmia.

Although in the illustrated embodiment the speaker 68 outputs a speech only during a predetermined duration in each physical-information-image displaying cycle, it is possible to output a speech simultaneously when each physical-information obtaining device 50, 52, 54 detects or reads a value of a corresponding sort of physical information.

It is to be understood that the present invention may be embodied with other changes, improvements, and modifications that may occur to those skilled in the art without departing from the scope and spirit of the invention defined in the appended claims.

What is claimed is:

1. An apparatus for informing an operator of an abnormality of a physical information obtained from a living subject, comprising:

an endoscope which is operable by the operator for carrying out an endoscopy on the subject;

a physical-information obtaining device which obtains said physical information from the subject under said endoscopy and outputs a physical-information signal representing the obtained physical information;

a signal converting device which converts said physical-information signal into an analog speech signal having a waveform representing a speech corresponding to said obtained physical information;

a speech-signal storing device which prestores a plurality of digital speech signals, wherein the signal converting device converts one of the digital speech signals which corresponds to said physical-information signal, into said analog speech signal having said waveform representing said speech corresponding to said obtained physical information;

a speech outputting device which outputs said speech represented by said analog speech signal;

judging means for judging whether said obtained physical information represented by said physical-information signal is abnormal; and a frequency shifting device which shifts, when said judging means makes a positive judgment, frequencies of said speech output by said speech outputting device, so that the operator is informed of the abnormality of the physical information obtained from the subject.

2. An apparatus according to claim 1, wherein said speech outputting device comprises a speaker.

3. An apparatus according to claim 2, wherein said speaker comprises a portable speaker which is adapted to be worn on the head of the operator.

4. An apparatus according to claim 3, wherein said portable speaker comprises at least one of an earphone and a headphone.

5. An apparatus according to claim 1, wherein said judging means comprises means for making said positive judgment that said obtained physical information is abnormal, when a measured value as said obtained physical information does not fall within a predetermined normal range.

6. An apparatus according to claim 1, wherein said physical-information obtaining device comprises at least one of a blood-pressure measuring device, a blood-oxygen-saturation measuring device, and a heart-rate measuring device.

7. An apparatus according to claim 1, wherein said frequency shifting device comprises means for shifting the frequencies of said speech up to higher frequencies, when said judging means makes said positive judgment.

8. An apparatus according to claim 1, wherein said frequency shifting device comprises means for modulating said speech signal provided by said signal converting device, thereby shifting the frequencies of said speech output by said speech outputting device.

9. An apparatus for informing an operator of an abnormality of a physical information obtained from a living subject, comprising:

an endoscope which is operable by the operator for carrying out an endoscopy on the subject;

a physical-information obtaining device which obtains said physical information from the subject under said endoscopy and outputs a physical-information signal representing the obtained physical information;

judging means for judging whether said obtained physical information represented by said physical-information signal is abnormal; and a portable vibrator which is adapted to be worn on the operator who carries out said endoscopy and which produces, when said judging means makes a positive judgment, a vibration which is transmitted to the operator so that the operator is informed of the abnormality of the physical information obtained from the subject under the endoscopy.

10. An apparatus according to claim 9, wherein said portable vibrator comprises means for producing said vibration having a frequency falling within a range of 1 to 100 Hz.

11. An apparatus according to claim 9, wherein said portable vibrator comprises an eccentric rotor whose center of gravity is eccentric with respect to an axis of rotation thereof, and an electric motor which rotates said rotor about said axis of rotation.

12. An apparatus according to claim 11, wherein said portable vibrator further comprises a wrist band which supports said rotor and said motor and which is adapted to be wound around a wrist of the operator.

13. An apparatus according to claim 9, wherein said judging means comprises means for making said positive judgment that said obtained physical information is abnormal, when a measured value as said obtained physical information does not fall within a predetermined normal range.

14. An apparatus according to claim 9, wherein said physical-information obtaining device comprises at least one of a blood-pressure measuring device, a blood-oxygen-saturation measuring device, and a heart-rate measuring device.

15. An apparatus according to claim 9, further comprising:

a signal converting device which converts said physical-information signal into an analog speech signal having a waveform representing a speech corresponding to said obtained physical information;

a speech outputting device which outputs said speech represented by said speech signal; and a frequency shifting device which shifts, when said judging means makes said positive judgment, frequencies of said speech output by said speech outputting device, so that the operator is informed of the abnormality of the physical information obtained from the subject.

16. An apparatus according to claim 15, further comprising a speech-output switch which is operable for selectively placing the speech outputting device in a first mode in which the speech outputting device outputs said speech and a second mode in which the speech outputting device does not output said speech.

17. An apparatus for informing an operator of an abnormality of a physical information obtained from a living subject, comprising:

an endoscope which is operable by the operator for carrying out an endoscopy on the subject;

a physical-information obtaining device which obtains said physical information from the subject under said endoscopy and outputs a physical-information signal representing the obtained physical information;

a signal converting device which converts said physical-information signal into an analog speech signal having a waveform representing a speech corresponding to said obtained physical information;

a speech outputting device which outputs said speech represented by said speech signal;

judging means for judging whether said obtained physical information represented by said physical-information signal is abnormal; and a frequency shifting device which shifts, when said judging means makes a positive judgment, frequencies of said speech output by said speech outputting device, so that the operator is informed of the abnormality of the physical information obtained from the subject.

18. An apparatus of claim 17, wherein said physical-information obtaining device comprises at least one of a blood-pressure measuring device, a blood-oxygen-saturation measuring device, and a heart-rate measuring device.

* * * * *